US012588850B2

(12) United States Patent
Laske et al.

(10) Patent No.: US 12,588,850 B2
(45) **Date of Patent: *Mar. 31, 2026**

(54) MONITORING AND ANALYSIS OF INVASIVE AND NON-INVASIVE ELECTROPHYSIOLOGICAL SIGNALS

(71) Applicant: CARDIOINSIGHT TECHNOLOGIES INC., Independence, OH (US)

(72) Inventors: Timothy G. Laske, Shoreview, MN (US); Qingguo Zeng, Solon, OH (US); Qing Lou, Solon, OH (US)

(73) Assignee: CARDIOINSIGHT TECHNOLOGIES INC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/827,011

(22) Filed: Sep. 6, 2024

(65) Prior Publication Data

US 2024/0423523 A1     Dec. 26, 2024

Related U.S. Application Data

(63) Continuation of application No. 17/935,982, filed on Sep. 28, 2022, now Pat. No. 12,089,939.

(Continued)

(51) Int. Cl.
*A61B 5/282*       (2021.01)
*A61B 5/339*       (2021.01)
*A61B 5/349*       (2021.01)

(52) U.S. Cl.
CPC .............. *A61B 5/282* (2021.01); *A61B 5/339* (2021.01); *A61B 5/349* (2021.01)

(58) Field of Classification Search
CPC ......... A61B 5/282; A61B 5/339; A61B 5/349; A61B 5/06; A61B 5/6852; A61B 5/4836;
(Continued)

(56) References Cited

U.S. PATENT DOCUMENTS 10,323,922 B2    6/2019  Zeng et al.
10,842,410 B2    11/2020  Kusumoto
(Continued)

FOREIGN PATENT DOCUMENTS

EP       3092944 B1      4/2020
GB       2510452 A       5/2014
WO       2014118535 A2   8/2014

OTHER PUBLICATIONS

Applicant: Cardioinsight Technologies Inc.; International Application No. PCT/US2022/078785 Filed Oct. 27, 2022; PCT International Search Report and Written Opinion; dated Feb. 24, 2023; 15 pgs.

(Continued)

*Primary Examiner* — Bo Joseph Peng
(74) *Attorney, Agent, or Firm* — Tarolli, Sundheim, Covell & Tummino LLP

(57) ABSTRACT

A computer-implemented method includes storing location data for at least one invasive electrode that is movable within a patient's body. The method also includes storing electrophysiological measurement data representing the electrophysiological signals measured at the outer surface of a patient's body by body surface electrodes and within the patient's body by the at least one invasive electrode. The method also includes storing geometry data representing anatomy of the patient spatially, and locations of the respective body surface electrodes and the at least one invasive electrode in three-dimensional space. The geometry data for the at least one invasive electrode can vary based on movement of the at least one invasive electrode within the (Continued)

patient's body. The method also includes reconstructing electrophysiological signals on a surface of interest within the patient's body based on the electrophysiological measurement data and the geometry data.

20 Claims, 7 Drawing Sheets

Related U.S. Application Data

(60) Provisional application No. 63/274,710, filed on Nov. 2, 2021.

(58) Field of Classification Search
CPC ... A61B 5/7264; A61B 5/7425; A61B 5/6805; A61B 5/367
See application file for complete search history.

(56) References Cited

U.S. PATENT DOCUMENTS

| | | | | |
|---|---|---|---|---|
| 2007/0232949 | A1 | 10/2007 | Saksena | |
| 2008/0009758 | A1* | 1/2008 | Voth | A61B 5/367 |
| | | | | 600/523 |
| 2015/0216438 | A1 | 8/2015 | Bokan et al. | |
| 2020/0273182 | A1 | 8/2020 | Raudins | |
| 2020/0345261 | A1* | 11/2020 | Haeusser | A61B 5/361 |
| 2021/0001116 | A1* | 1/2021 | Waldhauser | A61B 34/25 |
| 2022/0344025 | A1* | 10/2022 | Bort | A61B 5/367 |
| 2022/0386924 | A1* | 12/2022 | Denner | A61B 5/352 |
| 2023/0190104 | A1* | 6/2023 | Zeng | A61B 5/349 |
| | | | | 600/509 |
| 2023/0226361 | A1* | 7/2023 | Lou | G16H 50/50 |
| | | | | 604/503 |
| 2024/0148311 | A1* | 5/2024 | Cuervo | A61B 5/36 |

OTHER PUBLICATIONS

Laura R. Bear, PhD., et al. "How accurate is inverse electrocardiogramapping? A Systematic in Vivo Evaluation." Circulation: Arrhythmia and Electrophysiology vol. 11, No. 5; Apr. 26, 2018; 12 pgs.; https://doi.org/10.1161/CIRCEP.117.006108.
Yong Wang and Yoram Rudy, Application of the Method of Fundamental Solutions to Potential-based Inverse Electrocardiogramnals of Biomedical Engineering, vol. 34, No. 8, Aug. 2006; pp. 1272-1288; DOI: 10.1007/s10439-006-9131-7.

* cited by examiner

400

450

1000

STORE LOCATION DATA FOR INVASIVE ELECTRODE(S) — 1002

STORE ELECTROPHYSIOLOGICAL MEASUREMENT DATA — 1004

STORE GEOMETRY DATA — 1006

RECONSTRUCT ELECTROPHYSIOLOGICAL SIGNALS ON A SURFACE OF INTEREST — 1008

DETECT MOVEMENT OF INVASIVE ELECTRODE ? — 1010

MONITORING AND ANALYSIS OF INVASIVE AND NON-INVASIVE ELECTROPHYSIOLOGICAL SIGNALS

CROSS REFERENCE TO RELATED APPLICATION

This application is a continuation of U.S. application Ser. No. 17/935,982, filed Sep. 28, 2022, which claims the benefit of U.S. Provisional Patent Application No. 63/274,710, filed 2 Nov. 2021, each of which is incorporated herein by reference in its entirety.

FIELD

The present technology is generally related to monitoring and analysis of electrophysiological signals.

BACKGROUND

Electrocardiographic mapping (ECM) is a technology that is used to determine and display heart electrical information from sensed electrical signals. ECM can be performed based on invasive or non-invasive measurements of cardiac electrical activity. However, each of invasive measurements and non-invasive measurements can have limitations that may impact the electrophysiology data that is ultimately used in the diagnosis and treatment of cardiac arrhythmias.

SUMMARY

The techniques of this disclosure generally relate to using both invasive and non-invasive electrophysiological measurements for electrocardiographic mapping.

In one aspect, the present disclosure provides a system that includes an arrangement of body surface electrodes adapted to measure electrophysiological signals on an outer surface of a patient's body. The system also includes an invasive electrode adapted to measure electrophysiological signals within the patient's body. A signal monitoring device has inputs to receive to the electrophysiological signals measured on the outer surface of a patient's body and within the patient's body. The signal monitoring device is configured to provide electrophysiological measurement data representing the electrophysiological signals measured on the outer surface of the patient's body and the electrophysiological signals measured within the patient's body. A computing apparatus includes non-transitory memory to store data and instructions executable by a processor thereof. The data can include geometry data representing the anatomy of the patient spatially, and locations of the respective body surface electrodes and the invasive electrode in three-dimensional space. Geometry data for the invasive electrode can vary based on the movement of the invasive electrode within the patient's body. The instructions, which are executable by the processor, are programmed to reconstruct electrophysiological signals on nodes distributed across a surface of interest within the patient's body based on the electrophysiological measurement data and the geometry data, in which the electrophysiological measurement data representing the electrophysiological signals measured at the outer surface of a patient's body and within the patient's body.

In another aspect, the disclosure provides a computer-implemented method. The method includes storing location data for at least one invasive electrode that is movable within a patient's body. The method also includes storing electrophysiological measurement data representing the electrophysiological signals measured at the outer surface of a patient's body by body surface electrodes and within the patient's body by the at least one invasive electrode. The method also includes storing geometry data representing anatomy of the patient spatially, and locations of the respective body surface electrodes and the at least one invasive electrode in three-dimensional space. The geometry data for the at least one invasive electrode can vary based on movement of the at least one invasive electrode within the patient's body. The method also includes reconstructing electrophysiological signals on a surface of interest within the patient's body based on the electrophysiological measurement data and the geometry data.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
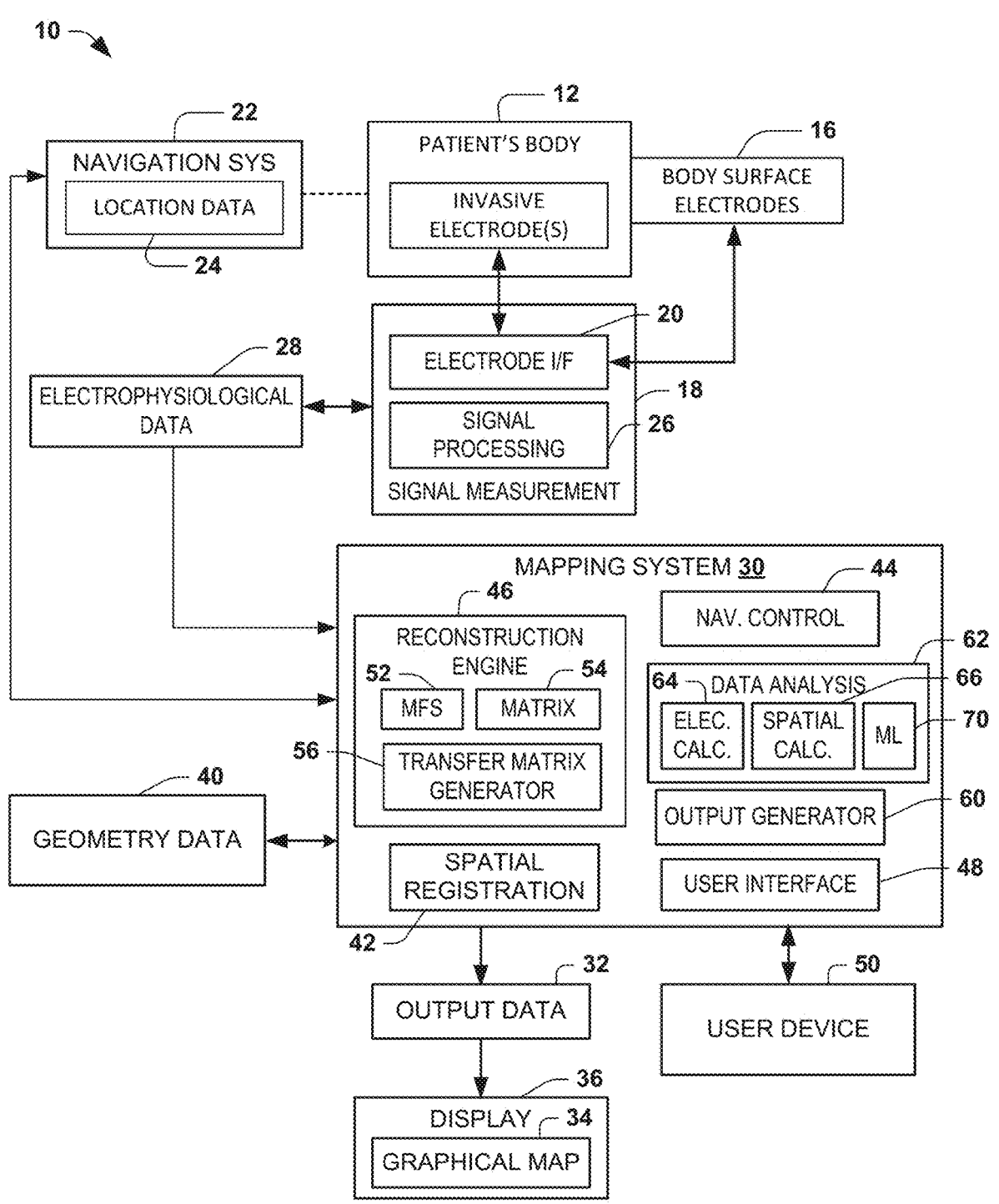
FIG. 1 is a block diagram that illustrates a system for monitoring and analyzing electrophysiological signals.

This disclosure relates to systems and methods for monitoring and analysis of electrophysiological signals, which may be measured invasively and non-invasively.

In an example, a system includes an arrangement of body surface electrodes adapted to measure non-invasively electrophysiological signals on an outer surface of a patient's body as well as an invasive electrode adapted to measure invasively electrophysiological signals within the patient's body (e.g., on or within the patient's heart). A signal processing device has inputs coupled to receive to the electrophysiological signals measured on the outer surface of a patient's body and within the patient's body and to provide electrophysiological measurement data. The electrophysiological measurement data thus represents both the electrophysiological signals measured on the outer surface of the patient's body and the electrophysiological signals measured within the patient's body. The electrophysiological measurement data can be stored in memory of a computing apparatus along with geometry data representing anatomy of the patient spatially and locations of the respective body surface electrodes and the invasive electrode in three-dimensional space. The computing apparatus also includes one or more processors configured to reconstruct electrophysiological signals on a surface of interest within the patient's body based on the electrophysiological measurement data and the geometry data. For example, the electrophysiological signals can be reconstructed onto an epicardial surface, endocardial surface, a transmural surface (e.g., at spatial locations between epicardial and endocardial surfaces) as well as any combinations thereof.

In some examples, the invasive electrode is mounted to a probe (e.g., catheter) that is moveable within the patient's body so that it can be used to measure electrophysiological signals at respective locations. The location of the probe can be determined by a localization system and the location can be updated as the probe is moved from a given location to a new location within the patient's body. The computing device can be configured to identify a region of interest based on the reconstructed electrophysiological signals on the surface of interest, and activation time (e.g., an activation map) can be determined for the region of interest. A site (e.g., one or more points) of earliest activation can be determined based on the electrophysiological signals within the region of interest. The earliest activation site or another site of interest determined from the reconstructed electrophysiological signals can be used to provide spatial guidance to a user, such as to instruct the user to move the probe to a target site, which may be the site of earliest activation or another site of interest. The electrophysiological signals can be measured at different locations within the region of interest and an updated electrocardiographic map can be generated based on the electrophysiological and geometry data.

In an example, the computing apparatus is programmed to compute the reconstructed electrophysiological signals using a method of fundamental solutions (MFS) in which each electrode (invasive and non-invasive) is represented mathematically according to its relative spatial location and signal measurement. As the probe is moved, the probe location data is updated from a previous location to a current location, and a portion of the mathematical representation for electrophysiological signals measured by the probe and its location is updated to reflect the current location and signal measurement. The computing apparatus can employ MFS to reconstruct the electrophysiological signals on the surface of interest updated mathematical representation and the electrophysiological signals.

In a further example, the computing apparatus can instruct a user to place the invasive electrode at a prescribed location within the patient's body in response to data indicating an ambiguity in electrophysiological signals on the surface of interest at or near the prescribed location. The prescribed location can represent a location that provides low amplitude signals or a signal otherwise difficult to sense from the body surface electrodes. The geometry data can be updated when the invasive electrode is at or near the prescribed location and electrophysiological signals can be reconstructed on the surface of interest based on the updated geometry data and the electrophysiological data, including the electrophysiological signals measured on the outer surface of the patient's body and the electrophysiological signals measured at or near the prescribed location. The resulting reconstructed electrophysiological signals can thus resolve or reduce the ambiguity and exhibit improved accuracy because the reconstruction is based on additional invasive electrophysiological signals at or near the prescribed location, which is determined or known a priori to influence the ambiguity.

FIG. 1 depicts an example of a system 10 for monitoring and mapping electrophysiological measurements from a patient 12. The system 10 includes one or more invasive electrodes 14 and body surface electrodes 16, which are coupled to a signal measurement device 18. For example, each of the electrodes 14, 16 is coupled to the signal measurement device 18 through a respective electrically conductive channel (e.g., including electrically insulated wires and/or traces) to communicate electrophysiological signals measured from the patient's body. The electrically conductive channels for the electrodes 14 and 16 can include an arrangement of connectors configured to couple to respective connectors (e.g., male and female connectors) of an electrode interface 20 of the measurement device 18. In other examples, the electrodes 14, 16 may be coupled to the electrode interface 20 through other forms of communication (e.g., optical fiber or wireless leads). The electrode interface 20 can measure unipolar, bipolar or a combination of unipolar and bipolar electrophysiological signals depending on the configuration of the measurement device 18 and processing of the signals measured by the electrodes 14 and 16. In the following examples, the electrophysiological signals are described as being cardiac signals measured by the electrodes 14, 16; however, the systems and methods disclosed herein are applicable to measure and process other types of electrophysiological signals (e.g., brain signals).

As an example, the one or more invasive electrodes 14 can be coupled to or otherwise carried by an electrophysiology probe. The probe can be a catheter that is moveable within the patient's body 12, such that the position of the probe and associated electrode(s) can vary. For example, the cardiac catheter can be inserted into a femoral vein and advanced to a position within the patient's heart. Alternatively, the probe and electrode(s) 14 can be configured to measure electrophysiological signals on an outer surface of the patient's heart. Thus, the signals measured by the invasive electrodes 14 depend on where the probe is positioned within the patient's body 12. The probe may be moved manually, robotically assisted or fully robotically.

The system 10 also includes a navigation system 22 configured to localize the spatial position of the invasive electrode 14. The spatial position of the electrode 14 (or associated probe) can be stored in memory as location data 24. The location data 24 thus represents a three-dimensional spatial position (e.g., spatial coordinates) of the electrode 14. Alternatively, the location data can represent the location of a sensor or other known location on the probe carrying the electrode(s), and the spatial location of each electrode 14 can be derived readily from the location data 24. The spatial location of the electrode(s) 14 can be with respect to the patient's body or a coordinate system of the navigation system 22. As described below, for example, the spatial location of the invasive electrode 14, which is described by or derived from the location data 24, can be registered with respect to anatomical geometry of the patient's body 12. The registration can be repeated in response to detecting changes in the location data as the electrode is moved within the patient's body. In some examples, the navigation system 22 can also generate the location data 24 to include the location of one or more of the non-invasive electrodes 16, which are distributed across an outer surface of the patient's body (e.g., on the thorax).

Useful examples of the navigation system 22 include the CARTO XP EP navigation system (commercially available from Biosense-Webster) and the ENSITE NAVX visualization and navigation technology (commercially available from Abbott); although other navigations systems could be used to provide the navigation data representative of the spatial position for the invasive electrode 14 and associated probe. Another example of a navigation system that can be utilized to localize the position of the invasive electrodes is disclosed in U.S. Pat. No. 10,323,922, issued Jun. 18, 2019 Aug. 29, 2014, and entitled LOCALIZATION AND TRACKING OF AN OBJECT, which is incorporated herein by reference. For example, a probe (e.g., catheter) can include one or more electrodes 14 disposed at known locations with respect to the probe. The probe can be used to position each such electrode 14 with respect to the heart and the navigation system 22 can determine corresponding three-dimensional coordinates for the electrode(s) 14 that is represented by the location data 24.

The number and placement of invasive electrodes 14 can vary depending upon the type of catheter or other probe to which the electrodes are coupled. In a further example, the invasive electrode(s) can be contact electrodes that measure signals from a surface of an object that the electrode physically engages or contacts. Alternatively, the invasive electrode(s) 14 can be non-contact electrodes that measure signals from a surface of an object while the electrode is spatially apart from (e.g., no physical contact between the electrode and the surface being measured).

The body surface electrodes 16 include a distributed arrangement of multiple electrodes (e.g., about 250 or more sensors) positioned on an outer surface of the patient's body 12. In an example, the body surface electrodes 16 are distributed completely around the thorax, such as can be mounted to a wearable garment (e.g., vest) in which each of the electrodes has a known location in a given coordinate system. For example, body surface electrodes 16 can be implemented as a non-invasive type of sensor apparatus as disclosed in U.S. Patent Publication No. 2013/0281814, entitled Multi-Layered Sensor Apparatus. Other configurations and numbers of body surface electrodes 16 could be utilized in other examples.

As described above, the electrode interface 20 has respective inputs coupled to each of the electrodes 14 and 16. The signal measurement device 18 can also include signal processing circuitry 26 configured to process electrical signals received by the electrodes 14, 16. The signal processing circuitry 26 can be implemented as hardware and/or software, such as including a digital signal processor and other processing circuitry and machine readable instructions (executable by a processor) configured to remove noise (e.g., line noise) and convert the received signals into a desired format for storing the measured electrophysiological signals as electrophysiological data 28. The signal processing circuitry 26 can also add channel information (e.g., to specify electrode number or location), add timestamps (e.g., to specify the time or each measurement sample) or perform other signal processing functions that may be desired. The electrophysiological data 28 thus can include signal measurement values for each sample as well as additional information, such as time stamps and channel information.

The system 10 also includes a mapping system 30 configured to generate output data 32, which may be used to render a graphical map (e.g., a map on a heart model) 34 and/or display processed electrical signals on a display 36. The mapping system 30 can also provide information in other display formats to provide guidance to the user representative of and/or derived from electrical activity that may be measured by any combination of the electrodes 14 and 16. The mapping system 30 can be a computer-implemented apparatus that includes one or more processors and memory to store data and machine-readable instructions, which are executable by the processor.

The mapping system 30 is programmed to generate the output data 32 based on the electrophysiological data 28 and geometry data 40. As described herein, for example, the output data 104 can represent or characterize electrophysiological signals on a surface of interest. For example, the surface of interest is a cardiac envelope, such as an epicardial surface, an endocardial surface, a combination of epicardial and endocardial surfaces of the patient's heart, a full thickness model of the heart or other three-dimensional geometrical surface (e.g., a sphere). The mapping system 30 may further generate the output data 32 to provide guidance to help a user move the invasive electrode 14 to a location of interest (e.g., one or near a region of interest of the heart) based on the electrophysiological data 28 and the geometry data 40, as disclosed herein.

The geometry data 40 includes electrode geometry data and anatomical geometry data. The electrode geometry data to represent spatial locations of respective body surface electrodes 16 and invasive electrode 14 in three-dimensional space. The anatomical geometry data represents spatial geometry of the surface of interest of the patient in three-dimensional space. The mapping system 30 can include a spatial registration function (e.g., machine-readable instructions) 42 programmed to co-register the electrode geometry data and the anatomical geometry data in a common coordinate system. The spatial registration function 42 can implement one or more transforms to align spatially respective data sets for location of the invasive electrodes 14, the location of the body surface electrodes 16 as well as the anatomical geometry for the surface of interest.

As an example, the navigation system 22 generates location data 24 to represent the spatial location of the invasive electrodes 14 in a given coordinate system (e.g., of the navigation system), which is typically different from the coordinate system in which the anatomical geometry data is generated. The anatomical geometry data can be derived from imaging data acquired by a three-dimensional medical imaging modality. In one example, an anatomical model can be constructed based on imaging data obtained (e.g., by a medical imaging modality) for the patient to provide spatial coordinates for points across the patient's heart and, in some cases, in which the electrodes 16 are positioned on the patient's body when the medical image is acquired, for the locations of the body surface electrodes 16 positioned on the outer surface of the patient's body. The medical imaging data can be generated for the patient's body using a medical imaging modality, such as multi-plane x-ray, computed tomography (CT), magnetic resonance imaging (MRI), ultrasound, positron emission tomography (PET), single-photon emission computed tomography (SPECT) and the like. The electrode locations and locations of the surface (or surfaces) of interest can be identified in a respective coordinate system of the acquired images through appropriate image processing, including extraction and segmentation. For instance, segmented image data can be converted into a two-dimensional or three-dimensional graphical representation that includes the volume of interest for the patient. Appropriate anatomical or other landmarks, including locations the electrode 14, can be identified in the geometry data 40 to facilitate spatial registration of the electrophysiological data 28. The identification of such landmarks can be done manually (e.g., by a person via image editing software) or automatically (e.g., via image processing techniques).

In another example, the location of the body surface electrodes 16 can be acquired by a digitizer, manual measurements or another non-imaging based technique, such as including being obtained by the navigation system 22 and included as part of the location data 24. The spatial registration function 42 can provide the geometry data 40 to include the location information for the electrodes 14 and 16 as well as the anatomical geometry all spatially aligned in the common coordinate system. Because the location of the invasive electrode can be moved within the patient's body 12, the corresponding location data 24 can be updated (e.g., in real-time or near-real time) to reflect the current spatial where the invasive electrical measurement is obtained. Thus, the spatial registration function 42 can further be programmed to update the geometry data in response to detecting change in the location data 24. The location data 24 can also include a time stamp so that the mapping system 30 can programmatically link (e.g., synchronize) a given time instance of the geometry data 40, which includes location of the electrode 14, with respective samples of the electrophysiological signals that are measured.

In a further example, the catheter or probe carrying the invasive electrode 14 can also include an imaging device to acquire images representing the anatomy of the patient. For example, the imaging device can be implemented as an optical camera, a dielectric camera, an optical coherence tomography device, an ultrasound transducer or other device integrated into or carried by the catheter or probe. The imaging device is configured to acquire images of anatomical feature intraoperatively, such as including all or part of the surface of interest or structure that is coupled to the surface of interest. The acquired images can be stored in memory as image data, such as in response to a user input to trigger image capture. The spatial registration function 42 can further be programmed to update and refine the geometry data based on the image data, such as to refine the surface of interest or other anatomy within the patient's body based on the invasively acquired images.

The mapping system 30 also includes a reconstruction engine 46 (e.g., instructions) programmed to compute reconstructed electrophysiological signals for locations on the surface of interest within the patient's body 12. In one example, the reconstruction engine 46 computes the reconstructed signals (e.g., electrical potentials) on the surface of interest by executing machine-readable instructions (e.g., an algorithm) to reconstruct electrical signals spatially and temporally on to the surface of interest based on the electrophysiological data (e.g., measurements from the electrodes 14 and 16) 28 and the geometry data 40 (e.g., including geometry data that is updated and/or refined, as described herein). As described herein, the geometry data 40 includes three-dimensional spatial information representing the surface (or surfaces) of interest describing a surface on to which reconstructed signals are computed (by engine 46) co-registered with respective locations where electrophysiological measurements are made (e.g., by the electrodes 14 and 16). The reconstruction engine 46 can calculate the reconstructed electrical signals on the surface of interest for one or more surfaces of interest over one or more time intervals. The time interval(s) may be selected through a user interface 48 in response to a user input entered by a user device 50 (e.g., mouse, keyboard, touchscreen interface, gesture interface or the like).

By way of example, the reconstruction engine 46 includes a transfer matrix generator 56 programmed to generate a transfer matrix 54 based on the geometry data 40. As described herein, the geometry data 40 used by the transfer matrix generator 56 includes information describing anatomical geometry of the surface of interest and geometry of the respective electrodes 14 and 16, which have been co-registered (e.g., by spatial registration function 42) in a common spatial coordinate system (e.g., with respect to patient anatomy). The anatomical geometry may be implemented as a mathematical model (e.g., a spline or mesh or point cloud) that defines locations (e.g., a point cloud) across the surface of interest. The electrode geometry can also be implemented as a model that defines spatial coordinates of the electrodes in the common coordinate system. As described herein, the electrode geometry of the invasive electrode 14 may change reflect movement of invasive electrode 14. The reconstruction engine 46 thus can employ transfer matrix 54 and the electrophysiological data 28 to reconstruct electrophysiological signals on the surface of interest.

As a further example, the reconstruction engine 46 includes code programmed to implement the method of fundamental solutions (MFS), shown as 52. The reconstruction engine 46 thus employs the MFS 52 to solve the inverse problem for computing reconstructed electrical signals on the surface of interest. MFS 52 includes a mathematical representation that spatially relates an influence of the electrophysiological signals measured on the outer surface of the patient's body and the electrophysiological signals measured within the patient's body to the electrophysiological signals at one or more regions of interest around heart. In an example, the MFS method 52 can implement MFS ECGI similar to that disclosed in U.S. Pat. No. 7,983,743, which is incorporated herein by reference, and further modified to utilize the electrophysiological data that includes measurements from both the invasive and non-invasive electrodes 14 and 16. Other useful examples of inverse algorithms that can be implemented by the reconstruction engine 46 to reconstruct include the boundary element method (BEM), such as disclosed in U.S. Pat. Nos. 6,772,004, and 9,980,660, each of which is incorporated herein by reference. The reconstruction engine 46 further may employ a regularization technique (e.g., Tikhonov regularization) to estimate values for the reconstructed electrical signals on the surface of interest.

The following example demonstrates use of MFS 52 to solve the inverse problem for reconstructing electrical signals on the surface of interest (e.g., as defined in geometry data 40), such as can be implemented by the reconstruction engine 46. For example, the reconstruction engine 46 can employ MFS 52 to estimate a solution of partial differential equations as a linear combination of fundamental solutions of the Laplacian operator, which constitutes a Cauchy problem for Laplace's equation having the following boundary conditions:

$$\begin{cases} \phi(x) = U_T(x) & x \in \Gamma_T, \text{ Dirichlet} \\ \phi(x) = B_T(x) & x \in \Omega, \text{ Dirichlet} \\ \dfrac{\partial U(x)}{\partial_n^v} & x \in \Gamma_T, \text{ Neumann} \end{cases}$$

where:

$U_T(x)$ represents unipolar signals on the body surface (e.g., measured by electrodes 16), $B_H(x)$ represents bipolar and/or unipolar signals acquired invasively from the heart (e.g., measured by electrodes 14 on a heart wall, intramural or near the wall).

In the context of MFS 52, the reconstruction engine can express potentials at each location can be expressed as follows:

$$u(r) = a_0 + \sum_i^M a_i f(r_i)$$

where $$f(r) = \frac{1}{4\pi r}$$

$$r = \|x - y\|$$

$$u(x) = a_0 + \sum_{y_i}^{N+K} a_i f(\|x - y_i\|)$$

As an example, suppose there are N unipolar electrodes located at $x_{ij}$, j=1, . . . , N on the body surface, and K bipolar measurements from respective bipolar channels. Bipolar signals $b(x_{hi})$ are the difference of signals from two nearby electrodes located at $x_{hi,1}$ and $x_{hi,2}$, where i=1, . . . , K. In one example, the transfer matrix generator 56 is programmed to generate the matrix 54 as a linear system of the inverse problem for bipolar channels as follows:

$$\begin{bmatrix}
1 & f(x_{t1}-y_1) & \cdots & f(x_{t1}-y_M) \\
1 & f(x_{t2}-y_1) & \cdots & f(x_{t2}-y_M) \\
\vdots & \vdots & \ddots & \vdots \\
1 & f(x_{tN}-y_1) & \cdots & f(x_{tN}-y_M) \\
0 & \frac{\partial f(x_{t1}-y_1)}{\partial \vec{n}} & \cdots & \frac{\partial f(x_{t1}-y_M)}{\partial \vec{n}} \\
0 & \frac{\partial f(x_{t2}-y_1)}{\partial \vec{n}} & \cdots & \frac{\partial f(x_{t2}-y_M)}{\partial \vec{n}} \\
\vdots & \vdots & \ddots & \vdots \\
0 & \frac{\partial f(x_{tN}-y_1)}{\partial \vec{n}} & \cdots & \frac{\partial f(x_{tN}-y_M)}{\partial \vec{n}} \\
0 & f(x_{h1,1}-y_1)-f(x_{h1,2}-y_1) & \cdots & f(x_{h1,1}-y_M)-f(x_{h1,2}-y_M) \\
0 & f(x_{h2,1}-y_1)-f(x_{h2,2}-y_1) & \cdots & f(x_{h2,1}-y_M)-f(x_{h2,2}-y_M) \\
\vdots & \vdots & \ddots & \vdots \\
0 & f(x_{hK,1}-y_1)-f(x_{hK,2}-y_1) & \cdots & f(x_{hK,1}-y_M)-f(x_{hK,2}-y_M)
\end{bmatrix}$$

$$\begin{bmatrix} a_0 \\ a_1 \\ \vdots \\ a_M \end{bmatrix} = \begin{bmatrix} u(x_{t1}) \\ u(x_{t2}) \\ \vdots \\ u(x_{tN}) \\ 0 \\ 0 \\ \vdots \\ 0 \\ b(x_{h1}) \\ b(x_{h2}) \\ \vdots \\ b(x_{hk}) \end{bmatrix}$$

In the above system of equations, each body surface electrode 16 corresponds to two rows in the matrix above—one for potential measurement, and another for the boundary condition on the current. Each bipolar channel corresponds to one of the middle rows. For bipolar channels with stable locations like CS catheters, in which the location of electrodes 14 remains fixed, the corresponding rows in the matrix 54 likewise remain unchanged. For catheters configured to move the electrode 14 relative to the patient's heart, the transfer matrix generator 56 is programmed to recalculate the matrix 54 so the corresponding rows representative of the electrode(s) location are updated when the catheter moves. In an example, the transfer matrix generator 56 is programmed to add rows corresponding to the new location of the electrode 14 based on the location data 24 provided by the navigation system 22. The transfer matrix generator 56 can also be programmed to remove rows that correspond to the channels representing a previous location of the electrodes 14 in response to detecting that the electrode 14 has moved. The reconstruction engine 46 is thus programmed to reconstruct the electrophysiological signals on the surface of interest according to the MFS 52 which includes a mathematical representation (matrix 54) for electrophysiological signals measured by electrodes 16 at respective locations on the outer surface of the patient's body and the electrophysiological signals measured by electrode 14 at a current location within the patient's body.

In some examples, such as for repeated rhythms in which beats used across different regions correspond to the same cardiac phases, the transfer matrix generator 56 can be programmed to keep previous measurements with the previous catheter location(s) and corresponding rows of the matrix, and to add new rows for the new measurements. Examples of repeated rhythms that can utilize this approach include normal sinus rhythms (NSR), AT or VT. The transfer matrix generator 56 can align the phases of the respective measurements with respect to body surface ECGs, such as via template matching methods. The body surface ECGs can be measured using the same electrodes or a subset thereof used to make the body surface measurements, or a separate set of ECG electrodes can be used in addition to the set of body surface electrode.

In another example, the transfer matrix generator 56, can provide the matrix 54, such as described above, to include respective unipolar channels for one or more invasive electrodes 14, such as when the location of a reference channel is known. For example, if the unipolar channel uses the external reference as one or more body surface electrodes 16, then the unipolar channels can simply correspond to potential measurements only, without imposing a boundary condition on current. If the unipolar channel uses an internal reference, then the transfer matrix generator 56 can create a row in the matrix in a similar way to that demonstrated above for bipolar channels, such as follows:

$$\begin{bmatrix}
1 & f(x_{t1}-y_1) & \cdots & f(x_{t1}-y_M) \\
1 & f(x_{t2}-y_1) & \cdots & f(x_{t2}-y_M) \\
\vdots & \vdots & \ddots & \vdots \\
1 & f(x_{tN}-y_1) & \cdots & f(x_{tN}-y_M) \\
0 & \frac{\partial f(x_{t1}-y_1)}{\partial \vec{n}} & \cdots & \frac{\partial f(x_{t1}-y_M)}{\partial \vec{n}} \\
0 & \frac{\partial f(x_{t2}-y_1)}{\partial \vec{n}} & \cdots & \frac{\partial f(x_{t2}-y_M)}{\partial \vec{n}} \\
\vdots & \vdots & \ddots & \vdots \\
0 & \frac{\partial f(x_{tN}-y_1)}{\partial \vec{n}} & \cdots & \frac{\partial f(x_{tN}-y_M)}{\partial \vec{n}} \\
0 & f(x_{h1,1}-y_1)-f(x_{h1,2}-y_1) & \cdots & f(x_{h1,1}-y_M)-f(x_{h1,2}-y_M) \\
0 & f(x_{h2,1}-y_1)-f(x_{h2,2}-y_1) & \cdots & f(x_{h2,1}-y_M)-f(x_{h2,2}-y_M) \\
\vdots & \vdots & \ddots & \vdots \\
0 & f(x_{hK,1}-y_1)-f(x_{hK,2}-y_1) & \cdots & f(x_{hK,1}-y_M)-f(x_{hK,2}-y_M) \\
0 & f(x_{c1}-y_1)-f(x_{uniref}-y_1) & \cdots & f(x_{c1}-y_1)-f(x_{uniref}-y_1) \\
0 & f(x_{c2}-y_1)-f(x_{uniref}-y_1) & \cdots & f(x_{c2}-y_1)-f(x_{uniref}-y_1) \\
\vdots & \vdots & \ddots & \vdots \\
0 & f(x_{cL}-y_1)-f(x_{uniref}-y_1) & \cdots & f(x_{cL}-y_1)-f(x_{uniref}-y_1)
\end{bmatrix}$$

US 12,588,850 B2

-continued $$\begin{bmatrix} a_0 \\ a_1 \\ \vdots \\ a_M \end{bmatrix} = \begin{bmatrix} u(x_{t1}) \\ u(x_{t2}) \\ \vdots \\ u(x_{tN}) \\ 0 \\ 0 \\ \vdots \\ 0 \\ b(x_{h1}) \\ b(x_{h2}) \\ \vdots \\ b(x_{hk}) \\ v(x_{c1}) \\ v(x_{c2}) \\ \vdots \\ v(x_{cL}) \end{bmatrix}$$

where: $x_{cj}$ represents the unipolar location, $x_{uniref}$ represents the reference location, and $v(x_{cj})$ represents the unipolar measurements.

Figure 2:
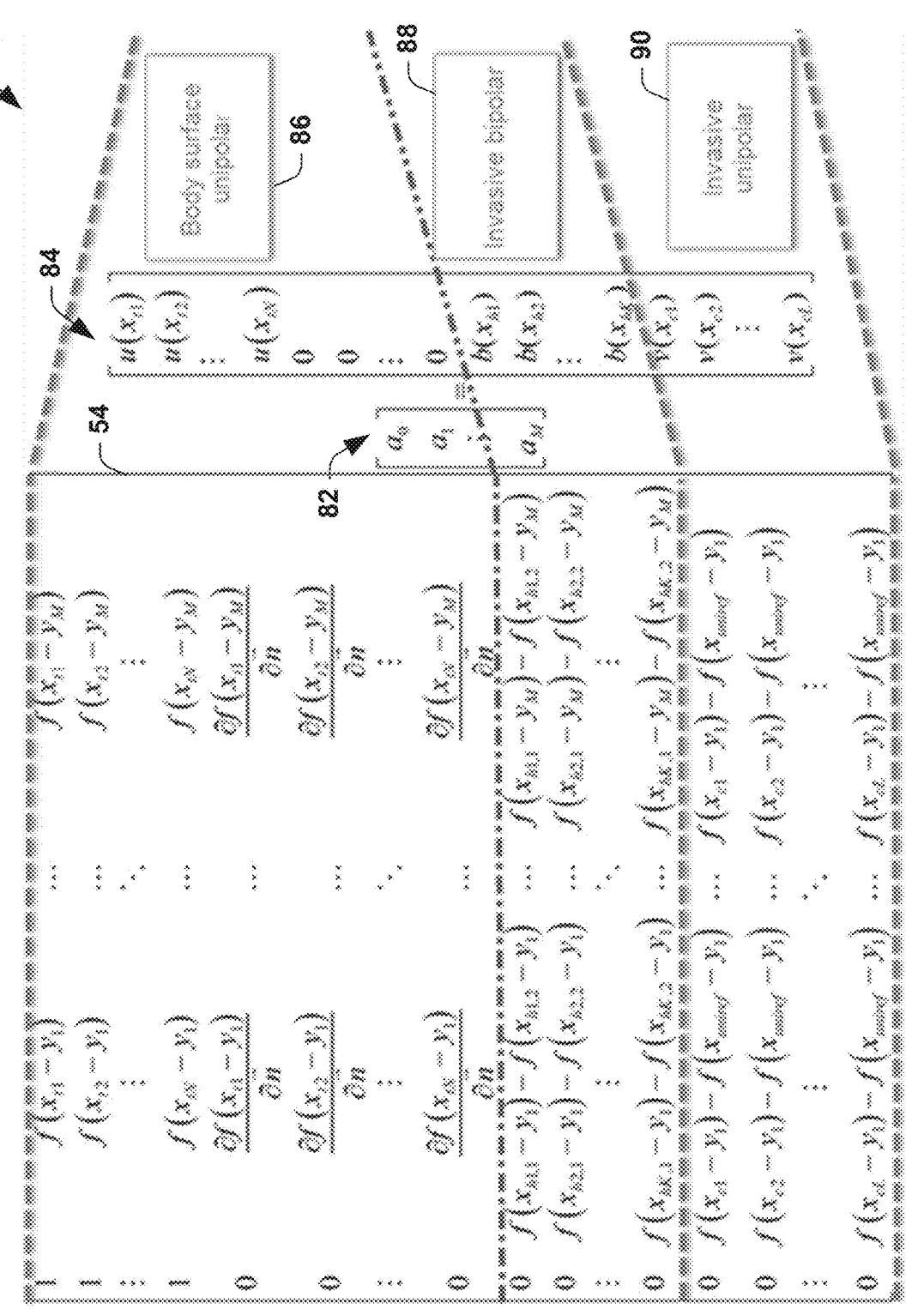
FIG. 2 is a mathematical expression showing an example of correspondence between portions of the expressions and measured electrophysiological signals.

As a further example, FIG. 2 depicts an example annotated system of equations 80 to show which rows of the transfer matrix 54 and other matrices 82 and 84 in the system of equations correspond to which types of signal measurements. In particular, the system shows, at 86 correspondence between portions of the matrix relating to body surface unipolar signals. The system 80 also shows at 88 which portions correspond invasive bipolar signals. The system 80 further shows at 90 which portions correspond invasive unipolar signals. For example, in response to the invasive electrode(s) 14 being moved, portions 88 and 90 of the matrix 54 would be updated (e.g., by transfer matrix generator) to represent the relative influence of the invasive measurements, which can vary as a function of the location of the electrode 14 for respective measurement samples, on the inverse solution for reconstructing electrophysiological signals on the surface of interest. As described herein, for example, the invasive measurements can be on the heart wall, intramural and/or near the heart.

In some examples, the transfer matrix generator can be configured to update the transfer matrix in response to detecting that the electrode 14 (or catheter carrying the electrode) has moved by at least a predetermined distance (e.g., 1 cm, 0.5 cm or other set distance), which may be programmable in response to a user input. The movement of the electrode can be tracked based on a difference between the current location data 24 and the location data that was used to provide the geometry data for the last reconstructed signals (e.g., implemented by the reconstruction engine 46). In this way, small variations in movement (or errors within the navigation system) do not trigger recalculation of the transfer matrix 54.

Returning to FIG. 1, the monitoring system 30 also includes an output generator 60 that is programmed to generate an EP map that can be rendered on the display 36 to graphically visualize the reconstructed electrical signals on the surface of interest. As disclosed herein, the surface of interest may be an epicardial surface, an endocardial surface, or a combination of an epicardial or endocardial surfaces. Additionally, the surface of interest can be a cardiac envelope, such as a surface residing between the center of a patient's heart and the body surface where the electrodes are positioned. The surface of interest may encompass the entire cardiac surface or one or more regions (epicardial or endocardial) of interest, such as described herein.

The output generator 60 thus provides the output data 32 that may be provided to the display 36 to visualize one or more electrocardiographic maps as well as other electrical information derived from the reconstructed electrical signals. For example, the output generator 60 is programmed to generate an EP map based on the reconstructed signals (generated by reconstruction engine). By including reconstructed electrical signals (derived from both non-invasive measurements) and invasively measured signals in a respective map, the respective map can more accurately visualize cardiac electrophysiological signals.

In a further example, the output generator 60 is programmed to generate output data 32 based on a data analysis function 62. The data analysis function 62 can include an electrical calculator function 64 and a spatial calculator function. Thus, the data analysis function 62 can perform calculations based on electrophysiological data 28, based on geometry data 40 or based on a combination or electrophysiological and spatial information.

As an example, the electrical calculator 64 is programmed to identify a region of interest based on the electrophysiological signals that have been reconstructed on the surface of interest (e.g., by reconstruction engine 46). The output generator can be configured to specify the region of interest in output data based on the identified ROI. Additionally, the navigation control 44 can be configured to provide location information (e.g., spatial coordinates on the surface of interest) so the navigation system can provide further guidance to help a user move the electrode 14 to the ROI. Electrophysiological data 28 can be recorded by the electrodes 14 and 16 at each location within the ROI. The reconstruction engine 46 can reconstruct electrophysiological signals across the surface of interest based on the electrophysiological data recorded at each site for one or more time intervals.

The electrical calculator 64 can compare the reconstructed signals across the surface of interest over the one or more time intervals (e.g., multiple beats) to locate a site of interest (e.g., a location having earliest activation or other electrophysiological parameter) on the surface based on electrophysiological signals measured by electrode 14 at different locations (recording sites) within the patient's body within the ROI. In an example, the electrical calculator 64 can be further programmed to evaluate reconstructed electrophysiological signals on the surface of interest within the patient's body and the electrophysiological signals measured by electrode 14 at the different locations within the patient's body over a common time range to determine the site of interest. The site of interest may be determined to include an epicardial surface, an endocardial surface or at a location or region within the myocardium between epicardial and endocardial surfaces.

Electrical data that includes measurements made outside the ROI can be discarded or otherwise excluded from reconstruction and/or comparison by the electrical calculator 64. The electrical data that includes measurements made outside the ROI can also be stored in memory for further analysis, such as if selected by the user interface 48 in response to a user input.

The data analysis 62 can further be configured to connect a site of rotational activity, fibrosis, and entrance or exit site for a ventricular tachycardia, or any region of electrophysiological interest with a corresponding location (a point or region) that can be further investigated with the invasive electrode(s) 14. The output generator 60 further can generate an updated map based on reconstructed electrophysiological signals on the surface of interest within the patient's body, including respective electrophysiological signals measured at the different locations within the patient's body within the region of interest.

In another example, the spatial calculator 66 is programmed to identify a prescribed location within the patient's body. The prescribed location can be identified in response to a user input specifying the location through the user interface 48. Additionally or alternatively, the prescribed location can be identified based on information indicating an ambiguity in electrophysiological signals on the surface of interest at or near the prescribed location. The information indicating the ambiguity can be generated by data analysis function 62, such as indicating low amplitude signals or differences among neighboring nodes within a region of interest or based on external information, such as from a medical images (e.g., cardiac echo, x-ray, CT scan or MRI). In an example, the output generator 60 can generate an output to instruct a user to place the invasive electrode at a prescribed location within the patient's body in response to data. The localization of the prescribed location to the user can further be guided based on the location data 24 generate by the navigation system 22, such as in response to instructions provided by navigation control 44. In another example, the information indicating the ambiguity is determined based on an analysis of the electrophysiological signals measured on the outer surface of the patient's body. Alternatively, or additionally, information indicating the ambiguity is determined based on the reconstructed electrophysiological signals or in response to a user input specifying an arrhythmia condition.

Additionally, the navigation control 44 can be programmed to cause the spatial registration function to update the geometry data 40 in response to detecting that the invasive electrode 14 is at or near the prescribed location within the patient's body. For example, the navigation control function 44 is programmed to compute a distance between a position of the electrode 14, which has been spatially registered (by spatial registration function 42) with patient anatomy (provided in geometry data), and the prescribed location. The distance can be computed by a number of pixels along a line connecting the electrode and the prescribed location, which can be translated to a physical distance. Alternatively, the navigation system 22 can be programmed to track the distance between the electrode and the prescribed location. The reconstruction engine 46 can then reconstruct the electrophysiological signals on a surface of interest based on the updated geometry data 40 and the electrophysiological data 28, including the electrophysiological signals measured on the outer surface of the patient's body and the electrophysiological signals measured at or near the prescribed location.

In another example, the data analysis function 62 is programmed to implement a machine learning (ML) model (e.g., machine-readable instructions executable by a processor) 70 pre-trained to automatically detect and classify one or more types of arrhythmias, such as premature ventricular contraction (PVC), premature atrial contraction (PAC), focal AT, re-entrant AT or others. For example, the ML model 70 can include of an artificial neural network (ANN) algorithm, a support-vector machine (SVM) algorithm, a decision tree algorithm, a recurrent neural network (RNN) algorithm, and a convolutional neural network (CNN) algorithm. Other types of machine learning can be used in other examples. The ML model 70 can be trained on prior identified electrocardiographic maps of interest from electrophysiological signals that represent one or more known categories of arrhythmias that occur during a respective time interval or a series of time intervals. The ML model 70 can be configured to process the reconstructed signals or resulting graphical maps, consistent with how the ML model is trained to identify respective trained categories of arrhythmia events. As a further example, the ML model 70 can be configured to evaluate respective input maps generated for a patient and label respective maps that are highly correlated (e.g., similar) to known training data to classify one or more categories of arrhythmias.

Figure 3:
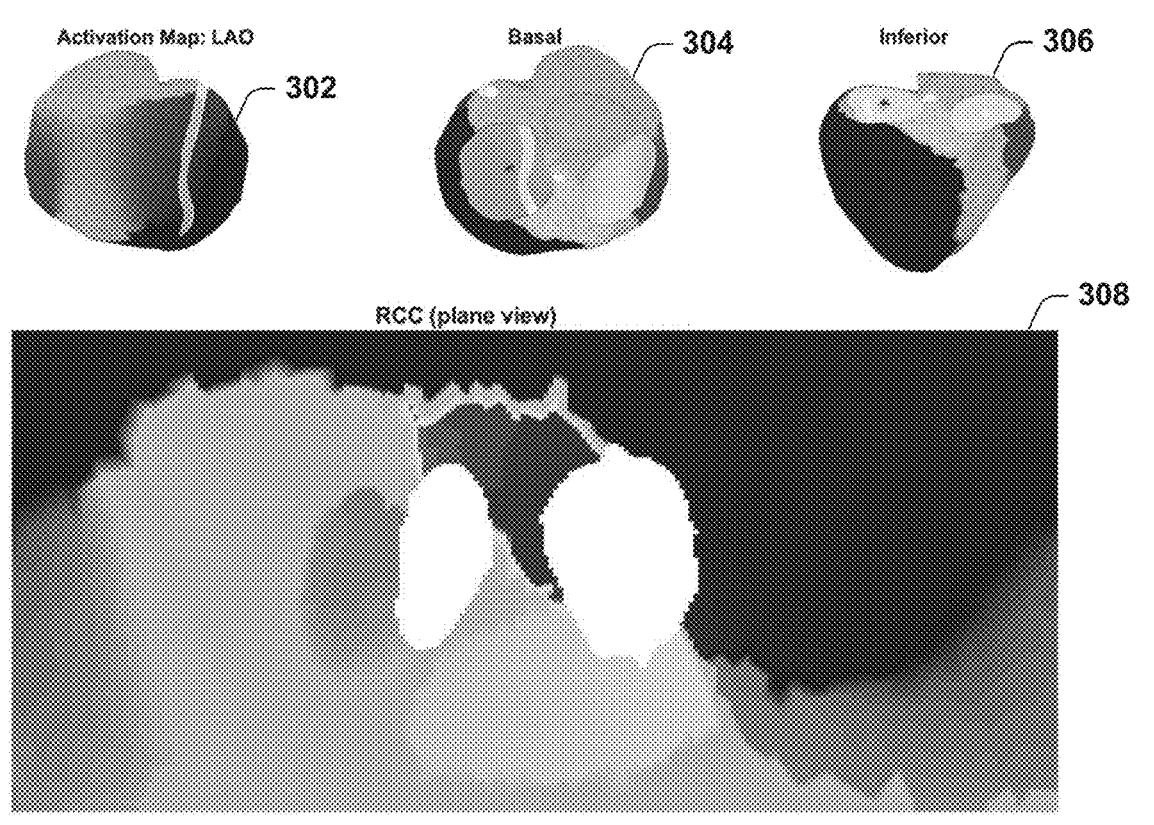
FIG. 3 is a set of ECGI maps that illustrate an example PVC event.
Figure 4:
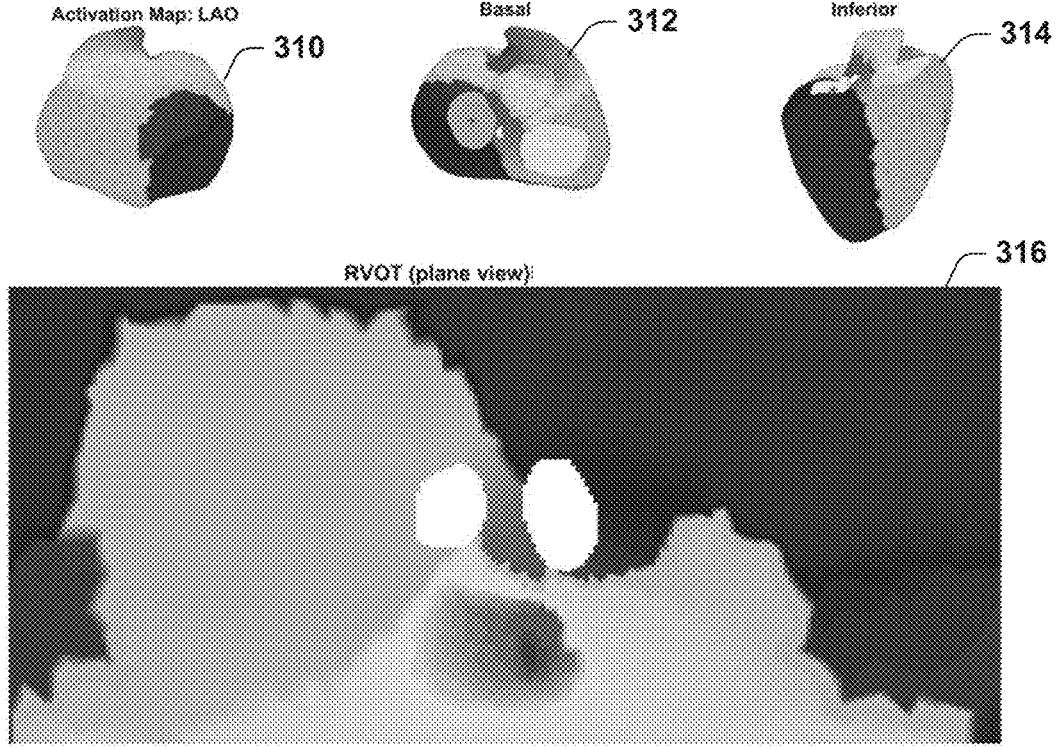
FIG. 4 is a set of ECGI maps that illustrate another example PVC event.
Figure 5:
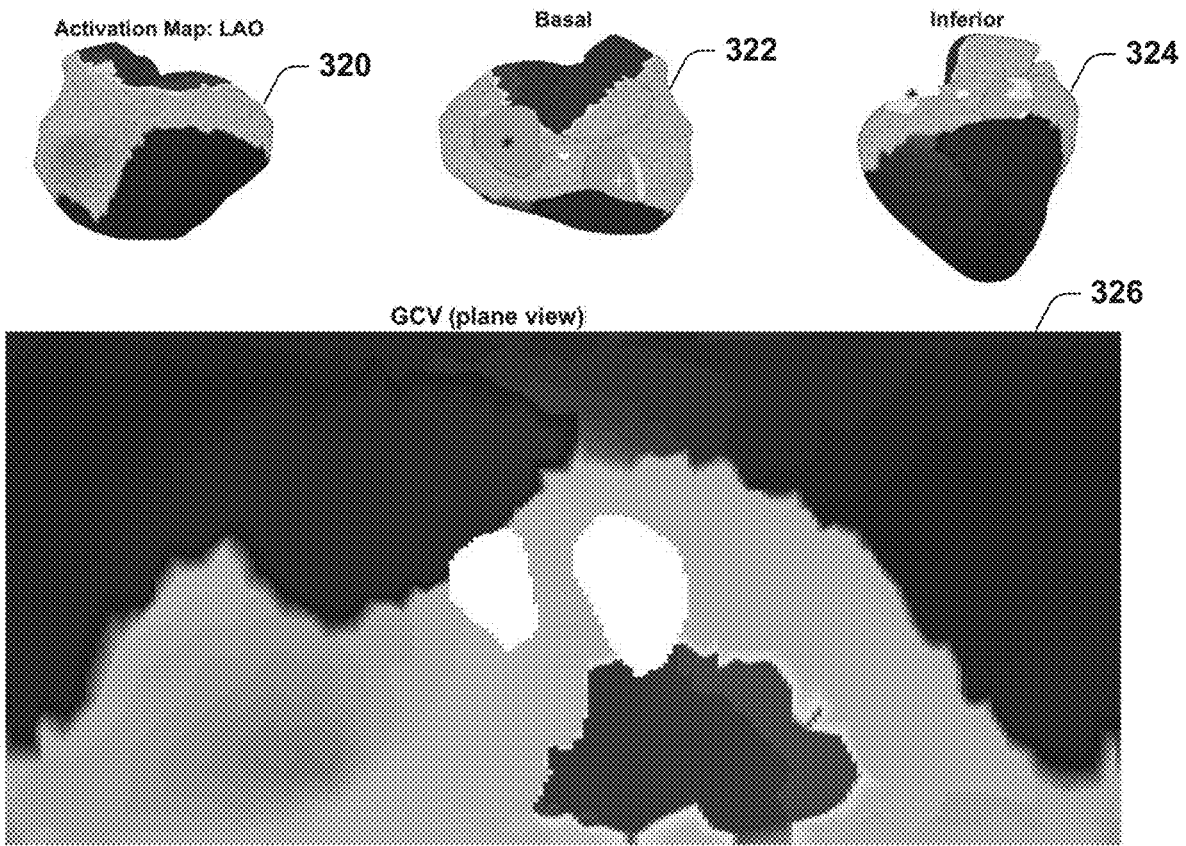
FIG. 5 is a set of ECGI maps that illustrate another example PVC event.

FIGS. 3-9 demonstrate an example of how machine learning can be implemented to detect automatically a given arrhythmogenic condition based on analysis of reconstructed electrical signals on a surface of interest (e.g., an ECGI map). In the example of FIGS. 3-9, the ML model 70 is trained to identify premature ventricular contractions (PVCs); however, the approach disclosed herein is equally applicable to detect and classify other types of arrhythmias. Each of FIGS. 3, 4 and 5 show respective maps having different views that have been generated (e.g., by reconstruction engine 46) and are known to exhibit PVCs. The PVC can be detected from a standard 12 lead ECG or another method. The maps generated for PVCs, such as shown in FIGS. 3, 4 and 5, thus include the time interval(s) when the known PVC event(s) occurs and define part of a set (e.g., library) of PVC images. For example, FIG. 3 depicts a case where the PVC occurs at the right coronary cusp (RCC). FIG. 3 shows three maps of a patient's heart from different angles including the left anterior oblique (LAO) view 302, the basal view 304 and inferior view 306. FIG. 3 also shows an enlarged plane view of the RCC at 308. FIG. 4 depicts an example of a PVC occurring at the right ventricular outflow tract (RVOT) and shows different map views, including LAO view 310, the basal view 312 and inferior view 314. An enlarged plane view of a map of the RVOT is also shown at 316. FIG. 5 depicts an example of maps when a PVC occurs at or near the great cardiac vein (GCV). FIG. 5 includes maps from different views including the LAO view 320, the basal view 322 and inferior view 324. An enlarged plane view of a map of the GCV is also shown at 326.

Figure 6:
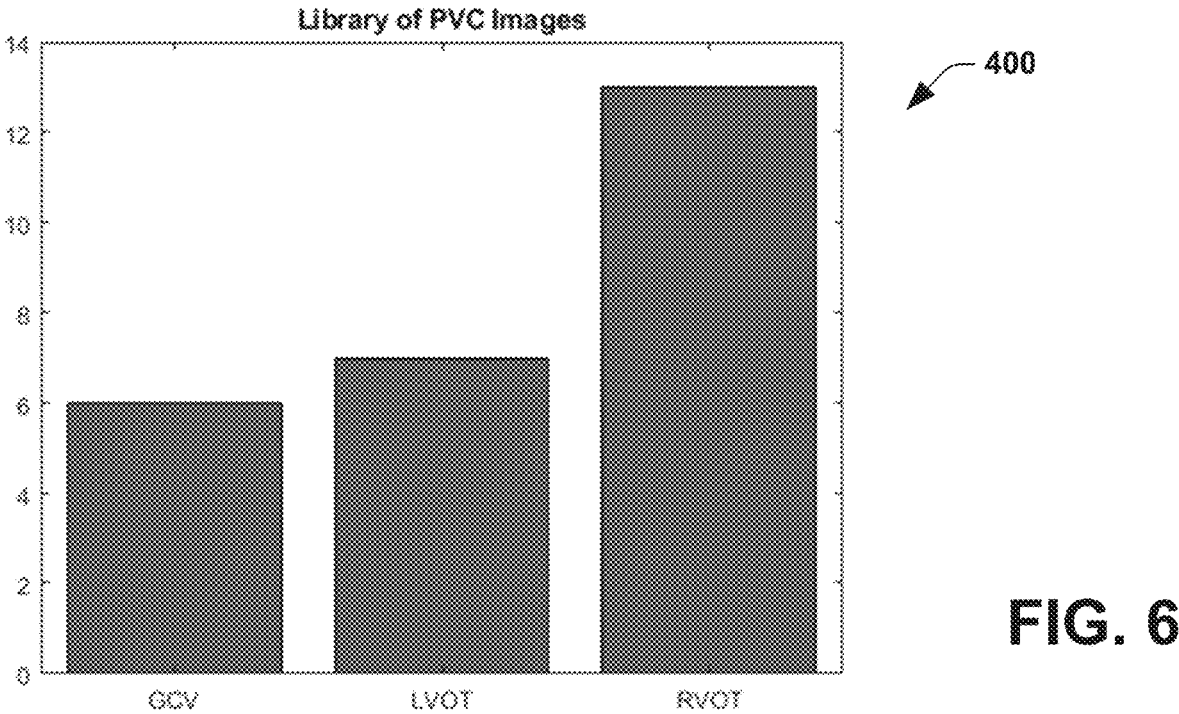
FIG. 6 is bar graph that illustrates an example library of PVC ECGI image data sets.
Figure 7:
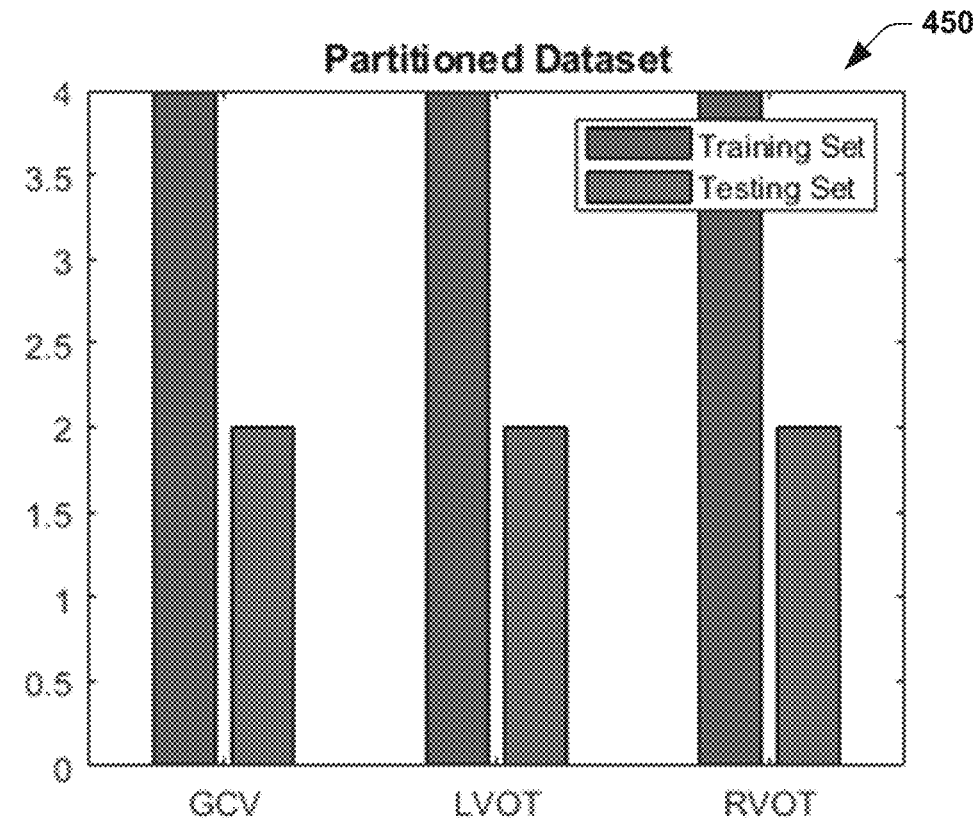
FIG. 7 is a graph that illustrates examples of partitioned data sets for training a machine learning model.
Figure 8:
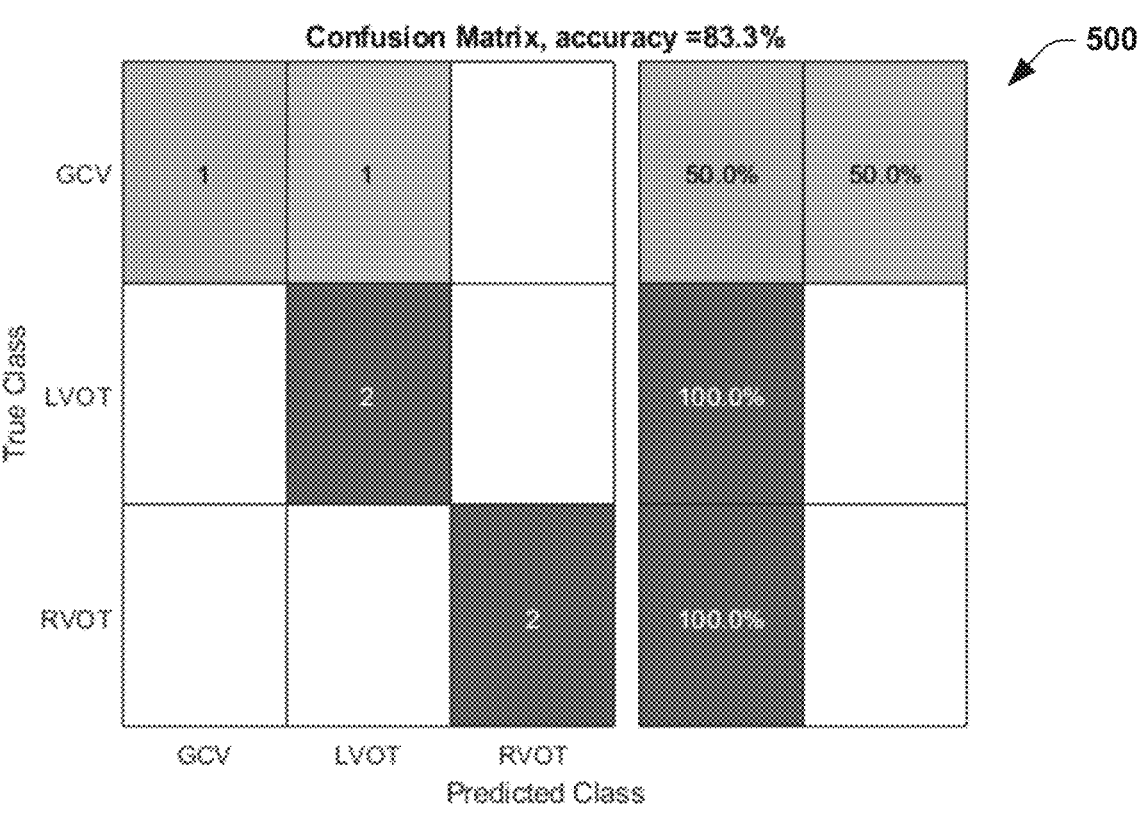
FIG. 8 is confusion matrix that illustrates performance of machine learning model trained to classify different categories of PVCs.

Multiple images of ECGI maps for PVCs that occur at specific locations can be collected and stored in library, such as the represented by the library 400 of FIG. 6 for GCV, LVOT and RVOT categories of PVC. As shown in FIG. 7, the ECGI image data sets from FIG. 6 can be partitioned into training and testing data sets for each category of PVC, such as shown at 450. The respective data sets can then be used to train the ML model to detect and classify each category of PVC. FIG. 8 depicts an example of a confusion matrix, showing an accuracy of about 83%. There typically will be greater numbers of images than shown in the examples of FIGS. 6 and 7 for use as training and testing data to generate the ML model and, the accuracy is expected to improve with a greater number of training and testing data.

Figure 9:
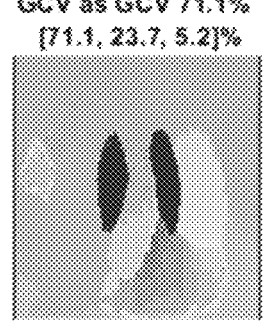
FIG. 9 is a set of ECGI maps that illustrate examples of classification of respective ECGI images for different categories of PVCs predicted by an example machine learning model.
Figure 9:
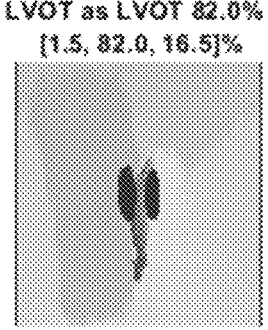
Figure 9:
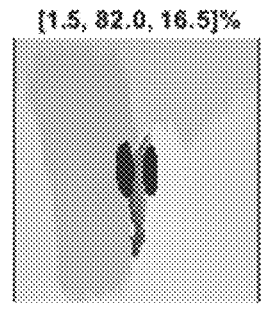
Figure 9:
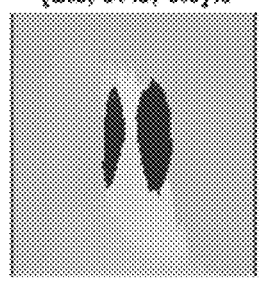
Figure 9:
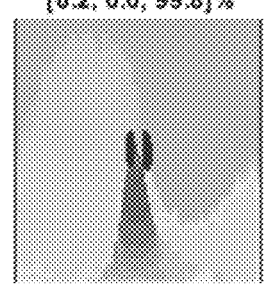
Figure 9:
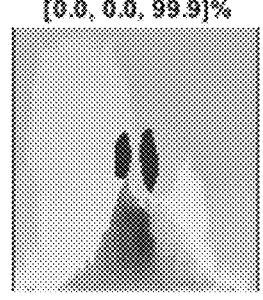

FIG. 9 shows output ECGI maps and confidence scores predicted for respective categories of PVCs (e.g., GCV, LVOT and RVOT) based on applying the trained model.

Figure 10:
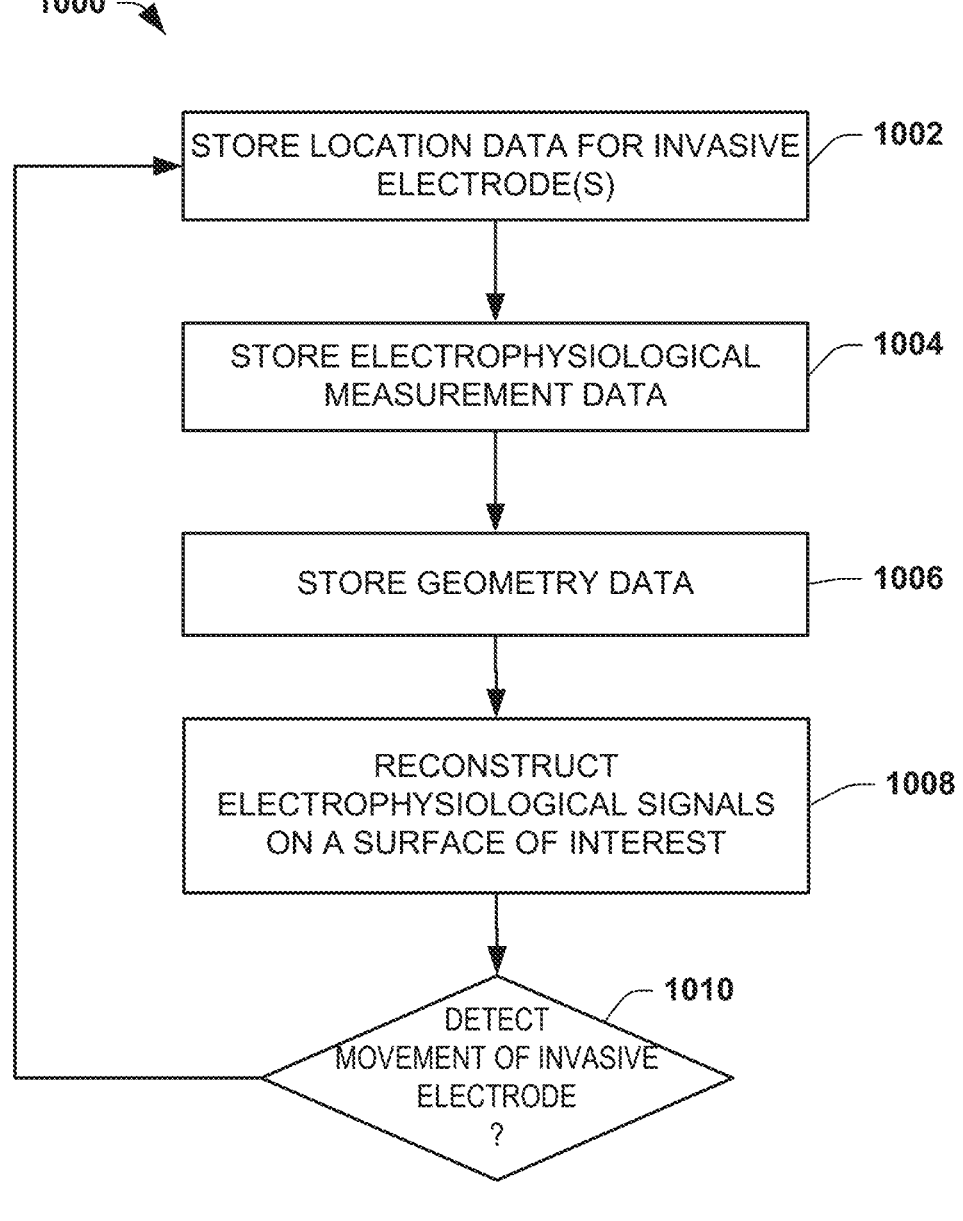
FIG. 10 is a flow diagram illustrating an example method for monitoring and analyzing electrophysiological signals.

FIG. 10 is a flow diagram that illustrates an example method 1000. While for purposes of simplicity of explanation, the example method of FIG. 10 is shown and described as executing serially, the example method 1000 is not limited by the illustrated order, as some actions could in other examples occur in different orders, multiple times and/or concurrently from that shown and described herein. Additionally, the method 1000 can be implemented as machine-readable instructions executed by a processor, such as by the mapping system 30. Accordingly, the description of FIG. 10 also refers to FIG. 1.

At 1002, the method includes storing location data for at least one invasive electrode that is movable within a patient's body. For example, navigation system 22 is configured to provide the location data representing the location of the invasive electrode in three-dimensional space. As disclosed herein, the at least one invasive electrode can be configured to move within the patient's body.

At 1004, the method includes storing electrophysiological measurement data representing the electrophysiological signals measured at the outer surface of a patient's body by body surface electrodes as well as within the patient's body by the at least one invasive electrode. For example, the signal measurement system 18 is configured to provide the electrophysiological measurement data 28, such as disclosed herein.

At 1006, the method includes storing geometry data representing anatomy of the patient spatially, and locations of the respective body surface electrodes and the at least one invasive electrode in three-dimensional space. The geometry data for the at least one invasive electrode is variable based on movement of the at least one invasive electrode within the patient's body. For example, spatial registration function 42 can register the location data with the patient anatomy and electrode locations to provide the geometry data. In an example, a probe to which the invasive electrode is coupled, can be configured to move within the patient's body, and the navigation/localization system updates the location data to represent a current location of the invasive electrode in the three-dimensional space. The signal processing circuitry 26 is similarly configured to update the electrophysiological measurement data to represent electrophysiological signals measured at the current location. In some examples, the probe or catheter to which the invasive electrode is coupled also includes an integrated imaging device, such as described herein. The optical imaging device can acquire images representing the anatomy of the patient, and the geometry data can be updated to refine the surface of interest or other anatomical structure within the patient's body based on the imaging data.

At 1008, the method includes reconstructing electrophysiological signals on a surface of interest within the patient's body based on the electrophysiological measurement data and the geometry data. For example, reconstruction engine 46 is configured to implement MFS 52 to reconstruct the electrophysiological signals on the surface of interest. MFS includes a mathematical representation (e.g., including matrix 54) that spatially relates (or characterizes) an influence of the electrophysiological signals measured on the outer surface of the patient's body and the electrophysiological signals measured within the patient's body to the electrophysiological signals on the surface of interest.

At 1010, the method includes detecting movement of the invasive electrode. For example, movement can be detected in response to navigation control 44 (or another function) determining a change in the spatial location of the invasive electrode. From 1010, the method returns to 1002 to update respective location data, electrophysiological measurement data and geometry data responsive to the current/new location of the invasive electrode. Based on the updated data, the method 1000 can reconstruct electrophysiological signals on the surface of interest within the patient's body.

For example, in response to the location data being updated from a previous location to the current location, a portion of the mathematical representation (matrix 54) can be removed for electrophysiological signals measured at the previous location and another portion be added to represent the current location where the electrophysiological signals are measured to provide an updated mathematical representation. The method can then reconstruct the electrophysiological signals on a surface of interest according to MFS with the updated mathematical representation.

The method 1000 further can implement other functions and features disclosed herein. For example, the method 1000 can use machine learning (ML model 70) to detect and classify one or more categories of arrhythmias. The method can also identify a region of interest based on analysis (e.g., by data analysis function 62) of the reconstructed electrophysiological signals on the surface of interest to locate a site of interest based on an analysis of signals measured at different locations within the patient's body within the region of interest. Examples that can be used for the site of interest include a site of earliest activation, a site of rotational electrical activity, a fibrosis, and entrance and/or exit site for a ventricular tachycardia, a previously ablated location, and a region with heterogeneous depolarization or repolarization. Other sites of interest to the user can also be used in other examples. The identified site of interest can be connected spatially with a corresponding location on the surface of interest to describe an electrophysiological circuit associated with the site of interest. An updated map can be generated based on reconstructed electrophysiological signals on the surface of interest within the patient's body, including respective electrophysiological signals measured at the different locations within the patient's body within the region of interest.

The method 1000 can also generate an output (e.g., graphical or other form of guidance) to instruct a user to place the at least one invasive electrode at a prescribed location within the patient's body in response to data indicating an ambiguity or another condition detected for electrophysiological signals on the surface of interest at or near the prescribed location. The geometry data can be updated (at 1006) in response to detecting that the invasive electrode is at or near the prescribed location within the patient's body, and the electrophysiological signals reconstructed on the surface of interest can be updated based on the updated geometry data and the electrophysiological data. The data indicating the ambiguity or other condition can be determined based on an analysis of the electrophysiological signals measured on the outer surface of the patient's body, the reconstructed electrophysiological signals or in response to a user input specifying an arrhythmia.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A system comprising:
   an arrangement of body surface electrodes adapted to measure electrophysiological signals on an outer surface of a patient's body;
   an invasive electrode adapted to measure electrophysiological signals within the patient's body;
   a computing apparatus including non-transitory memory to store data and instructions executable by a processor thereof, the data comprising:
      electrophysiological measurement data representing the electrophysiological signals measured on the outer surface of the patient's body and within the patient's body; and
      geometry data representing locations of the respective body surface electrodes and the invasive electrode in three-dimensional space, in which the geometry data for the invasive electrode is variable responsive to movement of the invasive electrode relative to the patient's body; and
   the instructions programmed to cause the processor to at least:
      reconstruct electrophysiological signals across a surface of interest within the patient's body based on the electrophysiological measurement data and the geometry data.

2. The system of claim 1, wherein the instructions are further programmed to cause the processor to classify one or more categories of arrhythmias based on the reconstructed electrophysiological signals.

3. The system of claim 1, wherein the instructions are further programmed to cause the processor to detect an arrhythmogenic condition based on analysis of the reconstructed electrophysiological signals at one or more respective locations across the surface of interest.

4. The system of claim 3, wherein the arrhythmogenic condition comprises a premature ventricular contraction.

5. The system of claim 1, wherein the instructions are further programmed to cause the processor to:
   train a machine learning model based on respective data sets that include or are derived from a plurality of reconstructed electrophysiological signals that correlate to one or more known categories of arrhythmias; and
   detect and classify at least one category of arrhythmia for the patient based on applying the machine learning model to the electrophysiological measurement data for the patient.

6. The system of claim 5, wherein the machine learning model is configured to implement at least one of an artificial neural network (ANN) algorithm, a support-vector machine (SVM) algorithm, a decision tree algorithm, a recurrent neural network (RNN) algorithm, and a convolutional neural network (CNN) algorithm.

7. The system of claim 1, wherein the instructions are further programmed to cause the processor to identify a region of interest within the surface of interest based on analysis of the reconstructed electrophysiological signals across at least a portion of the surface of interest.

8. The system of claim 7, wherein reconstructed signals across the surface of interest are reconstructed based on electrophysiological measurement data for electrophysiological signals measured over one or more time intervals, and the instructions are further programmed to cause the processor to compare the reconstructed signals across the surface of interest over the one or more time intervals to locate a site of interest based on an analysis of signals measured by the invasive electrode at different locations within the patient's body within the region of interest.

9. The system of claim 1, wherein the instructions are further programmed to cause the processor to:
   update the geometry data in response to movement of the invasive electrode from a first location to a second location; and
   reconstruct electrophysiological signals across the surface of interest based on the electrophysiological measurement data and the updated geometry data.

10. The system of claim 9, wherein the instructions are further programmed to cause the processor to:
   identify a region of interest based on the reconstructed electrophysiological signals on the surface of interest;
   locate a site of interest based on an analysis of signals measured at different locations within the patient's body within the region of interest; and
   connect the site of interest with a corresponding location on the surface of interest to describe an electrophysiological circuit associated with the site of interest.

11. The system of claim 1, wherein the instructions are further programmed to cause the processor to:
   instruct a user to move the invasive electrode to a prescribed location within the patient's body in response to detecting a condition on the surface of interest at or near the prescribed location;
   update the geometry data in response to changes in the location of the invasive electrode; and
   reconstruct the electrophysiological signals on the surface of interest based on the updated geometry data and the electrophysiological measurement data, including the electrophysiological signals measured on the outer surface of the patient's body and the electrophysiological signals measured at or near the prescribed location.

12. A computer-implemented method comprising:
   receiving electrophysiological measurement data representing electrophysiological signals measured by body surface electrodes at locations on an outer surface of a patient's body and by at least one invasive electrode that is movable relative to the patient's body;
   storing three-dimensional geometry data representing the locations of the body surface electrodes on the outer surface of the patient's body, a variable location for the at least one invasive electrode, and a spatial geometry of a surface of interest within the patient's body; and
   reconstructing electrophysiological signals on the surface of interest based on the electrophysiological measurement data and the geometry data.

13. The method of claim 12, further comprising classifying one or more categories of arrhythmias based on the reconstructed electrophysiological signals.

14. The method of claim 12, further comprising:

detecting an arrhythmogenic condition based on analysis of the reconstructed electrophysiological signals at one or more respective locations across the surface of interest.

15. The method of claim 12, further comprising:

training a machine learning model based on respective data sets that include or are derived from a plurality of reconstructed electrophysiological signals that correlate to one or more known categories of arrhythmias; and classifying at least one category of arrhythmia for the patient based on applying the trained machine learning model to the electrophysiological measurement data for the patient.

16. The method of claim 15, wherein the machine learning model is configured to implement at least one of an artificial neural network (ANN) algorithm, a support-vector machine (SVM) algorithm, a decision tree algorithm, a recurrent neural network (RNN) algorithm, and a convolutional neural network (CNN) algorithm.

17. The method of claim 12, further comprising:

instructing a user to place the invasive electrode at a prescribed location within the patient's body in response to detecting a condition on the surface of interest at or near the prescribed location;

updating the geometry data in response to changes in the location of the invasive electrode; and reconstructing the electrophysiological signals on the surface of interest based on the updated geometry data and the electrophysiological measurement data, including the electrophysiological signals measured on the outer surface of the patient's body and the electrophysiological signals measured at or near the prescribed location.

18. One or more non-transitory computer-readable media having instructions, which are executable by one or more processors, to cause the one or more processors to perform a method comprising:

accessing, from non-transitory memory, electrophysiological measurement data representing electrophysiological signals measured by body surface electrodes at locations on an outer surface of a patient's body and by at least one invasive electrode that is movable relative to the patient's body;

accessing, from the non-transitory memory, three-dimensional geometry data representing the locations of the body surface electrodes on the outer surface of the patient's body, a variable location for the at least one invasive electrode, and a spatial geometry of a surface of interest within the patient's body; and reconstructing electrophysiological signals on the surface of interest based on the electrophysiological measurement data and the geometry data.

19. The one or more non-transitory computer-readable media of claim 18, wherein the instructions are further executable to cause the one or more processors to:

classify one or more categories of arrhythmias based on the reconstructed electrophysiological signals for the patient.

20. The one or more non-transitory computer-readable media of claim 19, wherein the instructions are further executable to cause the one or more processors to:

train a machine learning model based on respective data sets that include or are derived from a plurality of reconstructed electrophysiological signals that correlate to one or more known categories of arrhythmias, wherein the one or more categories of arrhythmias are classified based on applying the trained machine learning model to the electrophysiological measurement data for the patient.

* * * * *